(12) United States Patent
Yang et al.

(10) Patent No.: US 9,980,906 B2
(45) Date of Patent: May 29, 2018

(54) SLOW AND CONTROLLED RELEASED LIPOSOMAL GEL COMPOSITION COMPRISING HYPOGLYCEMIC ACTIVE INGREDIENT AND METHOD OF PREPARING THEREOF

(71) Applicant: Hong Kong Baptist University, Hong Kong (HK)

(72) Inventors: Zhijun Yang, Hong Kong (HK);
Aiping Lu, Hong Kong (HK);
Zhaoxiang Bian, Hong Kong (HK);
Xiaoyu Chen, Hong Kong (HK);
Blenda Chi Kwan Wong, Hong Kong (HK)

(73) Assignee: Hong Kong Baptist University, Hong Kong (HK)

( * ) Notice: Subject to any disclaimer, the term of this patent is extended or adjusted under 35 U.S.C. 154(b) by 0 days. days.

(21) Appl. No.: 14/783,433

(22) PCT Filed: Oct. 20, 2014

(86) PCT No.: PCT/CN2014/088958
§ 371 (c)(1),
(2) Date: Oct. 9, 2015

(87) PCT Pub. No.: WO2015/123997
PCT Pub. Date: Aug. 27, 2015

(65) Prior Publication Data
US 2016/0074324 A1    Mar. 17, 2016

(30) Foreign Application Priority Data

Feb. 19, 2014    (CN) .......................... 2014 1 0055853

(51) Int. Cl.
*A61K 9/127*    (2006.01)
*A61K 9/06*    (2006.01)
(Continued)

(52) U.S. Cl.
CPC .............. *A61K 9/06* (2013.01); *A61K 9/0019* (2013.01); *A61K 9/127* (2013.01); *A61K 38/22* (2013.01);
(Continued)

(58) Field of Classification Search
CPC ...................................................... A61K 9/127
See application file for complete search history.

(56) References Cited

U.S. PATENT DOCUMENTS

| 7,164,005 | B2 | 1/2007 | Costantino et al. |
| 2005/0271702 | A1 | 12/2005 | Wright et al. |
| 2011/0212138 | A1* | 9/2011 | Houchin .............. A61K 9/0019 424/400 |

FOREIGN PATENT DOCUMENTS

| CN | 102198098 A | 9/2011 |
| CN | 101646424 | 3/2013 |
| CN | 102274182 | 4/2013 |

OTHER PUBLICATIONS

Escobar-Chavez et al (J Pharm Pharmaceutic Sci (9)3:339-358, 2006).*

(Continued)

*Primary Examiner* — Benjamin Packard
(74) *Attorney, Agent, or Firm* — Spruson & Ferguson (Hong Kong) Limited

(57) ABSTRACT

The present invention provides a slow and controlled released liposomal gel composition for subcutaneous administration comprises insulin or exenatide as active ingredient for reduction of blood sugar level and method of preparation thereof. Said controlled released composition has high bioavailability and is demonstrated to be able to sustain release therapeutically effective concentration of drug over a period of time and without rapid release of drug after initial administration. Method of preparing the controlled released composition of the present invention comprises the follow- (Continued)

ing steps: mixing insulin or exenatide, lipid and aqueous dispersion medium together; then mixing with poloxamer (e.g. F127 or P123) and/or gelatin and hyaluronic acid (HA) or the like gel solution so as to form a protective layer on surface of every lipid micro vesicles or nano-vesicles for use in intramuscular, abdominal and subcutaneous administration. A single administration of the present composition lasts 2 to 7 days to reduce side-effects, such as pain and irritation.

19 Claims, 4 Drawing Sheets

(51) Int. Cl.
| | |
|---|---|
| A61K 38/28 | (2006.01) |
| A61K 9/00 | (2006.01) |
| A61K 47/10 | (2017.01) |
| A61K 47/36 | (2006.01) |
| A61K 47/42 | (2017.01) |
| A61K 38/22 | (2006.01) |
| A61K 38/26 | (2006.01) |
| A61K 47/14 | (2017.01) |

(52) U.S. Cl.
CPC .............. *A61K 38/26* (2013.01); *A61K 38/28* (2013.01); *A61K 47/10* (2013.01); *A61K 47/14* (2013.01); *A61K 47/36* (2013.01); *A61K 47/42* (2013.01)

(56) References Cited

OTHER PUBLICATIONS

Baker, EN, Blundell, TL et al. The structure of Zn2+ pig insulin crystals at 1.5 A resolution. Philos. Trans. R. Soc. Lond. B Biol. Sci. 1988. 319:369-456.

Mitrakou A, Kelley D, Veneman T, et al. Contribution of abnormal muscle and liver glucose metabolism topostprandial hyperglycemia in NIDDM, Diabetes 1990; 39:1381-90.

Boehm B, Home P, Behrend C, et al. Premixed insulin aspart 30 vs. premixed human insulin 30/70 twice daily: a randomized trial in type 1 and type 2 diabetic patients. Diabet Med 2002; 19:393-399.

Bell DS, Importance of postprandial glucose control. South Med J 2001; 94:804-9.

Polonsky KS, Given BD, Hirsch LJ, et al. Abnormal patterns of insulin secretion in non-insulin dependent diabetes mellitus. N Engl J Med 1988; 318: 1231-9.

Pridal, et al., Glucagon-like peptide-1 (7-37) has a larger volume of distribution than glycagon-like peptide-1 (7-36) aminde in dogs and is degraded more quickly in vitro by dog plasma, Eur. J. Drug. Metab. Pharmacokinet., 21: 51-59, 1996.

Goke, et al., Exendin-4 is a high potency agonist and truncated exendin-(9-39)-aminde an antagonist at the glucagon-like peptide 1-(7-36)-amide receptor of insulin-secreting Beta-cells, J. Biol. Chem., 268: 19650-19655, 1993.

Schirra, et al., Gastric emptying and release of incretin hormones after glucose ingestion in humans, J. Clin. Invest t., 97: 92-103, 1996.

Greig et al., Once daily injection of exendin-4 to diabetic mice achieves long-term beneficial effects on blood glucose concentrations, Diabetologia 42: 45-50, 1999.

Chinese version of J. Senior, M. Radomsky, Sustained-release injectable products, 1st ed., Interpharm/CRC, New York, 2000, pp. 76-78.

Chan et al., Multi-vesicular lipid and applications, Clinical Medicine; 2007 (28) 170-173.

Jose MB., Mariko M., Kozo T. et al. Absorption of insulin from Pluronic F-127 gels following subcutaneous administration in rats. Int. J. Pharmaceutics. 1999 (184):189-198.

M. Brandl, U. Massing, Vesicular phospholipid gels, in: V.P. Torchilin, V. Weissig (Eds), Liposomes, 2nd ed., Oxford Press, New York, 2003, pp. 353-372.

Deacon et al., Dipeptidyl peptidase IV inhibition potentiates the insulinotropic effect of glucagon-like peptide 1 in the anesthetized pig, Diabetes, 47: 764-769, 1998.

"Liposome-collagen gel matrix: a novel sustained drug delivery system", Alan L. Weiner, et al., Journal of pharmaceutical sciences, vol. 74, No. 9, pp. 900-925.

Office Action of CN201410055853.5 issued from the State Intellectual Property Office of the People's Republic of China on Apr. 5, 2017.

\* cited by examiner

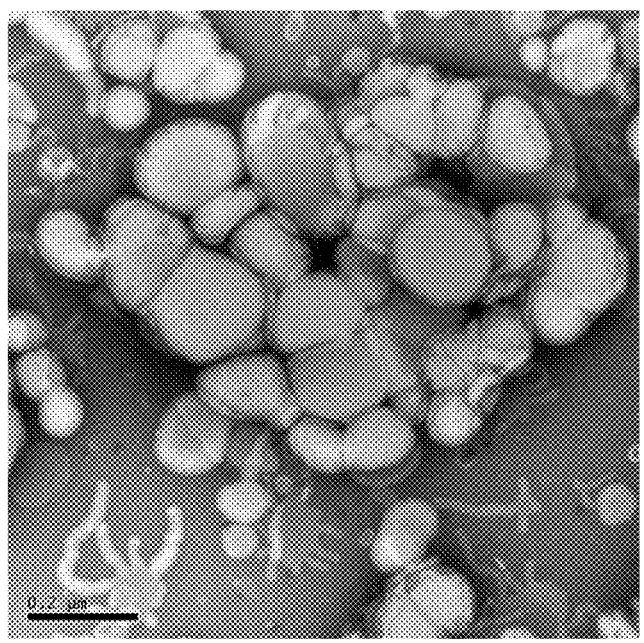
FIG. 1A
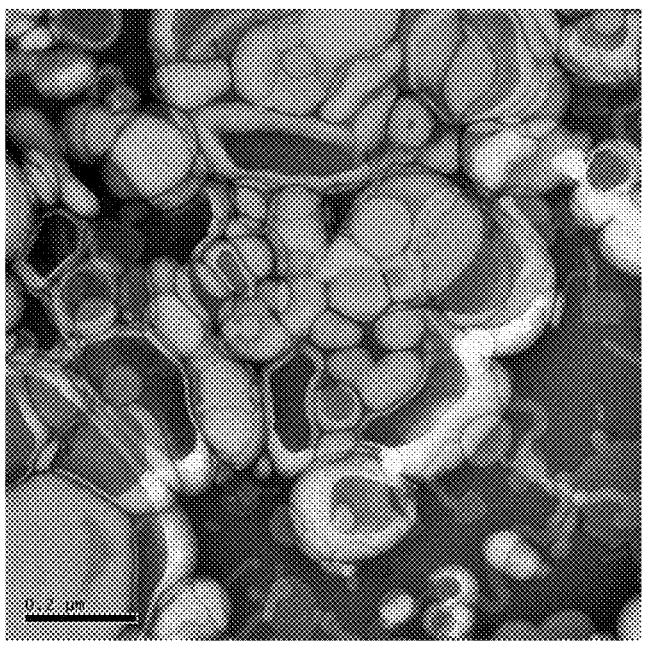
FIG. 1B
FIG. 1

SLOW AND CONTROLLED RELEASED LIPOSOMAL GEL COMPOSITION COMPRISING HYPOGLYCEMIC ACTIVE INGREDIENT AND METHOD OF PREPARING THEREOF

CROSS REFERENCE TO RELATED APPLICATION

The present application is a national phase application of the international patent application number PCT/CN2014/088958 filed on Oct. 20, 2014 which claims priority from Chinese Patent Application Number 201410055853.5 filed on Feb. 19, 2014, the disclosure of which is incorporated herein by reference in its entirety.

FIELD OF INVENTION

The present invention relates to a slow and controlled released liposomal gel composition including hypoglycemic active ingredient, such as insulin or exenatide, and method of preparing thereof.

BACKGROUND OF INVENTION

Insulin has been used clinically for diabetes treatment for decades; protein hormone insulin secreted by pancreatic islet β cells is particularly useful in regulating glucose metabolism and controlling blood sugar balance. Antigenicity of first generation of animal insulin is relatively high as amino acid sequence and structure of mammalian insulin molecule is slightly different; porcine insulin is the closest to human (Baker, E N, Blundell, T L et al. The structure of Zn2+ pig insulin crystals at 1.5 A resolution. Philos. Trans. R. Soc. Lond. B Biol. Sci. 1988. 319:369-456). Molecular weight of second generation human insulin is 5,808 Da, administration dosage can be reduced by approximately 30%; human insulin is relatively stable and can be stored at room temperature of 25° C. for about one month, and is reported to require to be administered 30 mins before meal. Insulin analogues are third generation insulin, which mimic human hypoglycemic action, can be administered just before meal and also known as prandial insulin or rapid-acting insulin.

Active pancreatic islet β cells first secrete proinsulin which made up of 84 amino acids, C chain of the proinsulin is cleaved under the action of pro-protein convertase (PC1 and PC2) and carboxypeptidase E and, C-terminus A chain and N-terminus B chain of the proinsulin join together via disulphide bond to become insulin. Insulin is stored in secretory vesicles of islet β cells as zinc ion coordinated insulin hexamer. Under glucose, lactose, ribose, arginine, glucagon stimulation, insulin is released from secretory vesicles into blood and exerts its physiological function. Insulin that maintains normal fasting blood glucose level is called basal insulin; insulin which reduces blood glucose level after meals to maintain normal blood glucose level is called prandial insulin. Prandial insulin suppresses generation of hepatic endogenous glucose to control the degree and time of blood glucose elevation after meal (Mitrakou A, Kelley D, Veneman T, et al. Contribution of abnormal muscle and liver glucose metabolism topostprandial hyperglycemia in NIDDM, Diabetes 1990; 39:1381-90). As a result, blood sugar level is controlled to near the fasting state level for the majority of time; and blood glucose level above 5.5 mmol/L would not last more than 30 mins (Boehm B, Home P, Behrend C, et al. Premixed insulin aspart 30 vs. premixed human insulin 30/70 twice daily: a randomized trial in type 1 and type 2 diabetic patients. Diabet Med 2002; 19:393-399). Pancreatic β islet cells in type 1 diabetes patients undergo autoimmune destruction which leads to reduction of basal and prandial insulin secretion. Pancreatic β islet cells in type 2 diabetes patients have an abnormal low functional efficiency leading to reduce insulin secretion (Bell D S, Importance of postprandial glucose control. South Med J 2001; 94:804-9), and resistant to insulin; normal fasting blood glucose and post prandial hyperglycemia continue for several hours to next meal (Polonsky K S, Given B D, Hirsch L J, et al. Abnormal patterns of insulin secretion in non-insulin dependent diabetes mellitus. N Engl J Med 1988; 318: 1231-9). Currently, treatment of type 2 diabetes includes analog formulation, such as Novolin N and Insulin Aspart. Type 1 diabetes treatment frequently uses insulin formulation with continuous pulse type insulin releasing pump to maintain a normal fasting blood glucose level. If blood sugar level cannot be effectively controlled through lifestyle and oral treatments, many turns to therapy with a basal insulin analogue, Insulin Detemir.

Byetta/Exenatide is a potent insulin secretion promoting drug, which is use in controlling blood sugar level in type 2 diabetes patients (T2DM), and is particularly useful for metformin, sulfonylurea and metformin sulfonylurea type patients that are more difficult to control blood sugar level. Exenatide has a half life of about two mins (much longer compared with mammalian glucagon-like peptide-1 (GLP-1) (Pridal, et al., Eur. J. Drug. Metab. Pharmacokinet., 21: 51-59, 1996; Deacon et al., Diabetes, 47: 764-769, 1998); is more resistant to proteolytic enzyme IV (dipeptide lactamase IV) degradation; has 53% amino acid sequence identity with GLP-1 (Goke, et al., J. Biol. Chem., 268: 19650-19655, 1993); is able to stimulate GLP-1 receptor, has an antidiabetic-effect related to GLP-1 receptor and has a similar role as GLP-1. Exenatide also enhances glucose-dependent insulin secretion and inhibits secretion of irregular high levels of glucose-dependent glucagon, slows down gastric emptying (Schira, et al., J. Clin. Invest t., 97: 92-103, 1996), reduces food intake, promote β cell proliferation and regeneration, reduce fat accumulation and insulin sensitizing effect (in animal model). Exendin-4 of Gila monster has a long blood sugar lowering effect (Greig et al., Diabetologia 42: 45-50, 1999). When exenatide is subcutaneously administered at 0.2 μg/kg or higher, it causes side-effects, such as vomiting, nausea, headache and the like.

Controlling the initial concentration of exenatide in blood and limiting initial release of exenatide are major barriers in the research and development for a controlled-released formulation of exenatide. U.S. Pat. No. 7,164,005 and Patent Application Publication US2005/0271702 and China Patent Application Publication CN101646424A disclose the use of exenatide containing nano-lipid gel capsule prepared by phase separation of poly(lactic-co-glycolic acid) (PLGA) copolymer. The preparation method includes phase separation method, spray drying method or the like. In addition, China Patent Application Publication CN102274182A discloses use of double emulsion solvent evaporation method to prepare exenatide multivescular liposomes. Although subcutaneous administration of exenatide multivesicular liposomes prepared from this method can control blood sugar level up to 7 days in rat, this method relies on the use of organic solvent and complex formulation that may cause skin irritation and the multivesicular liposome disclosed has a particle size of 5-50 μm. J. Senior et al. (J. Senior, M. Radomsky, Sustained-release injectable products, 1$^{st}$ ed., Interpharm/CRC, New York, 2000) points out that bigger the particle size of a lipid vesicle, the slower the subcutaneous release will be. Other literatures (Chan et al., Clinical Medicine; 2007 (28) 170-173) teach that multivesicular liposomes' particle size is too large for intravenous administration, settlement of liposome aggregate during storage which affects the stability of the formulation remains a problem, and existing liposome products are suspension and thus are difficult to store and transport. Additionally, large production of multivesicular liposome is difficult as the preparation thereof requires stringent production conditions, limiting the development of these liposomes. On Jan. 27, 2012, the FDA approved the weekly administration of exenatide extended-release injection formulation (Bydureon/Exenatide), weekly administration thereof is used as an adjuvant treatment for T2DM. The FDA requires pharmaceutical companies (Amylin) to establish a continuous registration system for severe risk of hypoglycemia, medullary thyroid carcinoma (MTC) and acute pancreatitis to analyze the annual rate of cancers caused by this treatment in the United States for at least 15 years, and to develop a set of risk assessment and mitigation strategies (REMS).

Apart from insulin calculating control pump, an insulin pump also requires an insulin reservoir, receiver tube, special needle and adhesive materials; needles and nozzle must also be changed frequently to prevent infection and blockage. Insulin pump is expensive, thus it is not covered by medical insurance and is frequently paid by patients themselves. Concentration of insulin used in insulin pump is 100 unit/ml, same concentration of human insulin cartridge. The use of insulin pump to administer insulin into subcutaneous tissue and the like, its absorption rate and curve is similar to the general subcutaneous insulin syringe. Decomposition of insulin hexamer into monomer in insulin solution is slow. Short-acting insulin dimer analogues decomposes into monomer rapidly, insulin pump requires administration of a 24 h dose distribution of basal insulin and additional dosage of insulin before meal. Adjustment of dosage is also required to prevent blood sugar level being too low. Insulin dosage also requires to be adjusted according to food intake and time. Adjustment of insulin dose often requires examination of the insulin pump from endocrinologist or service points. Jose M B et al. (Jose M B., Mariko M., Kozo T. et al. Absorption of insulin from Pluronic F-127 gels following subcutaneous administration in rats. Int. J. Pharmaceutics. 1999 (184):189-198) uses Pluronic hybrid hydrogels PF127 for the preparation of a sustained release insulin formulation for subcutaneous administration, but the drug concentration in blood and blood sugar concentration can only maintain for 12 hours in rats, and the formulation fails to provide a good sustained release. However, if merely increase the sustained release effects through increasing the concentration of PF127, skin irritation would increase.

In view of the foregoing, for insulin-dependent diabetic patients, there is a need for a development of a long acting, controlled release insulin formulation that is inexpensive, stable, low irritation to skin and easy for mass production for a safe, effective and compliance treatment.

SUMMARY OF INVENTION

The present invention provides a biocompatible, slow and controlled release liposome gel composition comprises hypoglycemic active ingredient, such as insulin or exenatide. Said composition is a high bioavailability controlled release composition for subcutaneous administration, wherein the release of active ingredient for blood sugar reduction, such as insulin or exenatide, is effectively controlled. The present invention also provides method of preparing said controlled released composition for subcutaneous administration.

Subcutaneous administration of the slow and controlled release liposome gel composition of the present invention exhibits high bioavailability and an initial rapid minimal dose drug delivery profile. A single administration of the present composition is able to provide a therapeutically effective amount of hypoglycemic active ingredient, such as insulin or exenatide, for 2-7 days or longer in vivo. The controlled release composition of the present invention comprises therapeutically effective amount of hypoglycemic active ingredient, lipid, thermoreversible gel and aqueous dispersion medium. Said thermoreversible gel is selected from poloxamer hydrogel, thiol-terminated poloxamer, gelatin, hyaluronic acid (HA), HA-dopamine conjugate and a combination thereof.

In one embodiment, the present invention provides a slow and controlled release liposome composition, said composition comprises therapeutically effective amount of hypoglycemic active ingredient, lipid, thermoreversible gel and aqueous dispersion medium; said thermoreversible gel is selected from poloxamer hydrogel, thiol-terminated poloxamer, gelatin, hyaluronic acid, HA-dopamine conjugates and a combination thereof.

In another aspect, the thermoreversible gel is poloxamer hydrogel and/or thiol-terminated poloxamer in a combination with gelatin, hyaluronic acid, HA-dopamine conjugates or a combination thereof. In another aspect, the thermoreversible gel is poloxamer hydrogel and/or thiol-terminated poloxamer in combination with hyaluronic or HA-dopamine conjugate. In yet another aspect, the thermoreversible gel is poloxamer hydrogel and/or thiol-terminated poloxamer in combination with hyaluronic acid. In another aspect, the thermoreversible gel is poloxamer hydrogel and/or thiol-terminated poloxamer in combination with gelatin and HA-dopamine conjugate. In another aspect, the thermoreversible gel is poloxamer hydrogel and/or thiol-terminated poloxamer in combination with hyaluronic acid and HA-dopamine conjugate. In another aspect, the thermoreversible gel is poloxamer hydrogel and/or thiol-terminated poloxamer in combination with gelatin, hyaluronic acid and HA-dopamine conjugate.

In one embodiment, the poloxamer hydrogel is poloxamer F127 or P123.

In one embodiment, concentration of thermoreversible gel of the present composition is 0.05% to 50%, 0.5%-35%, 1%-20%, 5%-15% or 10%-12% by weight.

In another embodiment, when the thermoreversible gel is poloxamer hydrogel and/or thiol-terminated poloxamer in combination with a second thermoreversible gel component selected from gelatin, hyaluronic acid, HA-dopamine conjugate or a combination thereof as described above, the concentrations of the poloxamer hydrogel and/or thiol-terminated poloxamer and said second thermoreversible gel component are 10-30% and 0.05-2% by weight, 15-25% and 0.08-1% by weight, 18-20% and 0.1-0.5% by weight or 20% and 0.1% by weight, respectively. In another embodiment, the concentrations of the poloxamer hydrogel in combination with the second thermoreversible gel component is 10-30% and 0.05-2%, 15-25% and 0.08-1%, 18-20% and 0.1-0.5% or 20% and 0.1%, by weight, respectively.

In another embodiment, lipid is selected from the group consisting of phospholipid, glycolipid, sterol, glyceride and fat-soluble vitamins. In the present liposome composition, the lipid is 0.05-50%, 0.7-30%, 1-20%, 1-10% or 2-5% by weight.

In another embodiment, in the present liposome composition, the hypoglycemic active ingredient is insulin, exenatide, liraglutide, pramlintide or a combination thereof. In another embodiment, insulin is one or more selected from the group consisting of insulin analogue, human insulin and animal insulin. Exenatide is one or more selected from the group consisting of Exendin-3, Exendin-4, C-terminus amide substituted Exenatide derivative, non-substituted Exenatide derivative and pharmaceutically acceptable salts thereof.

In another embodiment of the present invention, the hypoglycemic active ingredient is 0.01-2.5% by weight of the present composition.

In another embodiment of the present composition, the aqueous dispersion medium is selected from pure water suitable for administration, amino acid type buffer solution, polypeptide type buffer solution and pH buffer solution.

In another embodiment of the present invention, the lipid forms into vesicular lipid gels of 50 nm-20 μm in diameter, liposome suspension, W/O/W type emulsion or a homogeneous mixture; the hypoglycemic active ingredient is loaded or dispersed in the lipid and the lipid loaded or dispersed with hypoglycemic active ingredient is loaded into the thermoreversible gel.

In another aspect, the present liposome composition is capable to sustainably releases hypoglycemic active ingredient for 2-7 days or longer.

In another embodiment, the present invention provides a method of preparing slow and controlled release hypoglycemic active ingredient-containing liposome gel composition, said method comprises mixing therapeutically effective amount of hypoglycemic active ingredient, lipid and aqueous dispersion medium together to obtain lipid vesicles, liposome suspension, W/O/W type emulsion or homogeneous mixture having the hypoglycemic active ingredient loaded or dispersed therein; and emulsifying said lipid vesicles, liposome suspension, W/O/W type emulsion or homogeneous mixture by adding said lipid vesicle, liposome suspension, W/OW type emulsion or homogeneous mixture to thermoreversible gel solution; and forming liposomal microcapsule or nanocapsule, wherein said thermoreversible gel is selected from poloxamer hydrogel, thiol-terminated poloxamer, gelatin, hyaluronic acid, HA-dopamine conjugate and a combination thereof.

In another embodiment, said thermoreversible gel consists of poloxamer hydrogel and/or thiol-terminated poloxamer in combination with gelatin, hyaluronic acid, HA-dopamine conjugate or a combination thereof. In another embodiment, said thermoreversible gel consists of poloxamer hydrogel and/or thiol-terminated poloxamer in combination with hyaluronic acid or HA-dopamine conjugate. In yet another embodiment, said thermoreversible gel consists of poloxamer hydrogel and/or thiol-terminated poloxamer and hyaluronic acid. In another embodiment, said thermoreversible gel consists of poloxamer hydrogel and/or thiol-terminated poloxamer and HA-dopamine conjugate. In another embodiment, said thermoreversible gel consists of poloxamer hydrogel and/or thiol-terminated poloxamer, hyaluronic acid and HA-dopamine conjugate.

In one embodiment, the poloxamer hydrogel is poloxamer F127 or P123.

In one embodiment, concentration of thermoreversible gel of the present composition is 0.05%-50%, 0.5%-35%, 1%-20%, 5%-15% or 10%-12% by weight.

In another embodiment, when the thermoreversible gel is poloxamer hydrogel and/or thiol-terminated poloxamer in combination with a second thermoreversible gel component selected from the group consisting of gelatin, hyaluronic acid, HA-dopamine conjugate or a combination thereof as described above, the concentrations of the poloxamer hydrogel and/or thiol-terminated poloxamer and said second thermoreversible gel component are 10-30% and 0.05-2% by weight, 15-25% and 0.08-1% by weight, 18-20% and 0.1-0.5% by weight or 20% and 0.1% by weight, respectively. In another embodiment, the concentrations of the poloxamer hydrogel in combination with said second thermoreversible gel component is 10-30% and 0.05-2%, 15-25% and 0.08-1%, 18-20% and 0.1-0.5% or 20% and 0.1%, by weight, respectively.

In another embodiment, lipid is selected from the group consisting of phospholipid, glycolipid, sterol, glyceride and fat-soluble vitamins. In the present liposome composition, the lipid is 0.05-50%, 0.7-30%, 1-20%, 1-10% or 2-5% by weight.

In another embodiment, in the present liposome composition, the hypoglycemic active ingredient is insulin, exenatide, liraglutide, pramlintide or a combination thereof. In another embodiment, insulin is one or more selected from the group consisting of insulin analogue, human insulin and animal insulin. Exenatide is one or more selected from the group consisting of Exendin-3, Exendin-4, C-terminus amide substituted Exenatide derivative, non-substituted Exenatide derivative and pharmaceutically acceptable salts thereof.

In another embodiment of the present invention, the hypoglycemic active ingredient is 0.01-2.5% by weight of the present composition.

In another embodiment of the present composition, the aqueous dispersion medium is selected from pure water suitable for administration, amino acid type buffer solution, polypeptide type buffer solution and pH buffer solution.

In another embodiment, the present method further comprises drying the liposomal microcapsule or nanocapsule to obtain hypoglycemic active ingredient-containing lipid microcapsule or nanocapsule powder. In one embodiment, said drying step comprises phase separation, drying-spraying or freeze-drying.

In one embodiment, the present invention provides a hypoglycemic active ingredient-containing liposomal microcapsule or nanocapsule powder prepared by the method of the present invention.

Those skilled in the art will appreciate that the invention described herein is susceptible to variations and modifications other than those specifically described.

The invention includes all such variation and modifications. The invention also includes all of the steps and features referred to or indicated in the specification, individually or collectively, and any and all combinations or any two or more of the steps or features.

Unless otherwise defined, all technical terms used herein have the same meaning as commonly understood to one of ordinary skill in the art to which the invention belongs.

Other and advantages of the invention will be apparent to those skilled in the art from a review of the ensuing description.

BRIEF DESCRIPTION OF DRAWINGS

FIG. 1 shows electron micrographs of dehydrated lipid capsule of vesicular lipid gel (VLG) containing hypoglycemic active ingredient insulin (FIG. 1A) or Exenatide (FIG. 1B)

DETAILED DESCRIPTION OF INVENTION

Figure 2:
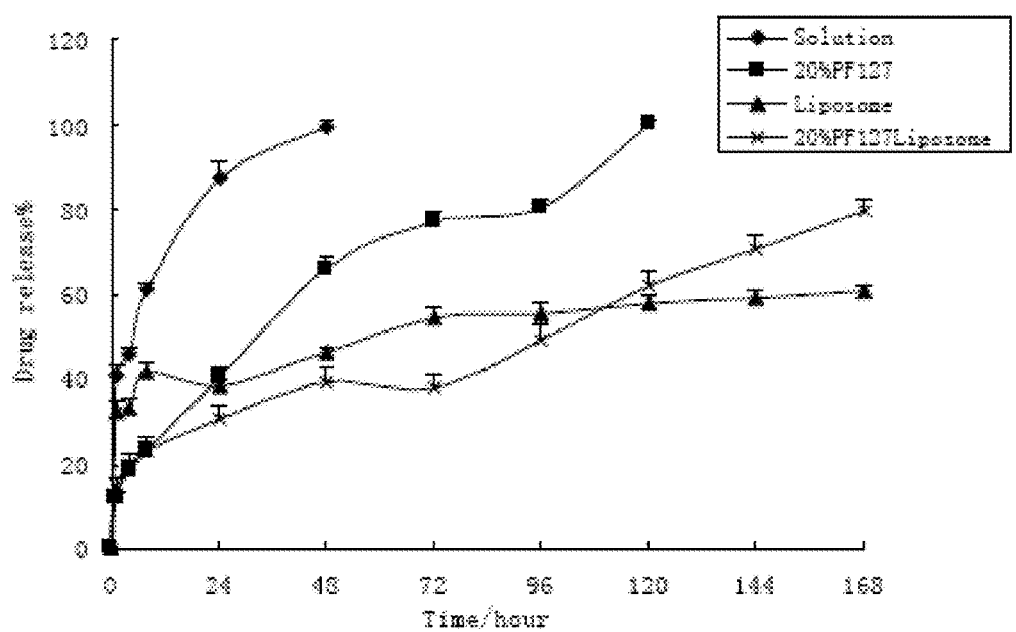
FIG. 2 shows release profile of insulin ex vivo

The following embodiments are described to more clearly to illustrate the present invention and additional advantages associated therewith.

The present invention provides a slow and controlled release liposome composition containing hypoglycemic active ingredient suitable for subcutaneous administration. Subcutaneous administration of the slow and controlled release liposome composition of the present invention exhibits high bioavailability and an initial rapid minimal dose drug delivery profile. The present liposome composition has good flowability at room temperature suitable for subcutaneous administration.

Hypoglycemic active ingredients applicable to the present invention include insulin, exenatide, liraglutide, pramlintide and a combination thereof.

In the present invention, insulin may be one ore more of the insulin selected from the group consisting of insulin analogues (also known as insulin similitude), such as insulin aspart, insulin aspart 30 and insulin detemir; human insulin, such as Novolin insulin series; and animal insulin. These insulins can be characterized by their duration of action from rapid-acting insulin analogues, short-acting insulin, intermediate-acting insulin, long-acting insulin (including long-acting insulin analogues) to premixed insulin (including premixed insulin analogues).

Exenatide of the present invention may be one or more of the exenatides selected from the group consisting of Exendin-3, Exendin-4, and functional fragments, derivatives and pharmaceutically acceptable salts thereof.

The phrase "therapeutically effective amount" as used herein refers to an amount, when compared to subject that has not received said amount, that leads to the following effects: improve treatment of a disease or disorder, healing, preventing or alleviating, or ameliorate side effects, or reduce the progression of a disease or disorder. In this aspect, the hypoglycemic active ingredient, such as insulin and exenatide, containing slow and controlled release liposome composition of the present invention comprises 0.01-2.5% by weight of hypoglycemic active ingredient, including 0.05%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4% or 2.5%. The therapeutically effective amount of hypoglycemic active ingredient may be readily determined by those skilled in the art.

In another embodiment, the lipid applicable to the present invention includes, but is not limited to, phospholipids, such as phosphatidylcholine, phosphatidyl inositol, phosphatidyl serine, phosphatidyl ethanolamine, bis-phosphatidyl glycerol, sphingomyelin, preferably phosphatidylcholine; glycolipids, such as cerebrosides, gangliosides, glucocerebroside and other sphingoglycolipids and glyceroglycolipid; sterols, such as β-sitosterol, campesterol; esters, such as lauric acid monoglyceride, stearic acid monoglyceride and other monoglycerides, and diglycerides, like 1-palmitoyl-2oleoyl-glycerol; and fat-soluble vitamins (e.g. vitamin A, D, E and K). These substances are harmless to human, and when injected, they are absorbed slowly, degraded and excreted. In another embodiment, the present liposome gel composition is prepared by vesicular lipid gels (VLG) method. Said method includes shear-homogenizing, under high pressure (e.g. 100-10,000 psi, such as 500, 1,000, 5,000, 8,000 or 10,000 psi) and high speed (e.g. 2,000-20,000 rpm, such as 5000, 10,000 or 15,000 rpm), aqueous solution of high concentration active ingredient (e.g. 0.1%-30% or 0.1%-20% by weight of the VLG) with lipid (having substantially equal weight percentage as the active ingredient) to form a paste of lipid vesicles; diluting the lipid vesicle paste in an aqueous medium to form liposomes. The liposomes are single component liposome, with small and uniform particle size of nano ranges (M. Brandl, U. Massing, Vesicular phospholipid gels, in: V. P. Torchilin, V. Weissig (Eds), Liposomes, $2^{nd}$ ed., Oxford Press, New York, 2003, pp. 353-372), to enable the liposome suspension exhibits good drug release profile and stable at the same time. In another embodiment, the injectable, slow and controlled release liposome gel composition of the present invention comprises 0.5-50%, 0.7-30%, 1-20%, 1-10% or 2-5% lipid by weight of the composition. In a preferred embodiment, the lipid is phosphatidylcholine. In one embodiment, the lipid may be a mixture of phospholipids, such as soy lecithin SPC, purified phospholipid, such as disteraoyl phosphatidyl ethanolamine (DSPE), or a combination thereof.

In one aspect, the thermoreversible gel suitable for use in the present invention may be poloxamer hydrogel (also known as Pluronic or Pluronic hybrid hydrogel), e.g. F127, P123. The thermoreversible gel is a transparent aqueous solution at room temperature or lower, at 37° C. body temperature, the thermoreversible gel forms a semi-solid gel to store and slowly release the active ingredient. The thermoreversible gel suitable for use in the present invention may be thiol-terminated/thiol end capped poloxamer (e.g. 1-thiol Pluronic), gelatin, hyaluronic acid (HA), HA-dopamine conjugate (L-DN-HA) and the like. The thermoreversible gel for use in the present invention can also be a combination of the above-mentioned examples. In one aspect, the injectable, slow and controlled release liposome composition of the present invention comprises according to weight of the composition approximately 0.05-50%, 0.5-35%, 1-20%, 5-15%, 10-12% of thermoreversible gel. In one aspect, the thermoreversible gel of the present invention is poloxamer hydrogel, such as F127, in combination with gelatin. In one embodiment, the poloxamer hydrogel and gelatin are 10-30% and 0.5-2%, preferably are 15-25% and 0.08-1%, preferably are 18-20% and 0.1-0.5%, and preferably are 20%-0.1%, respectively, by weight of the composition. In another embodiment, the poloxamer hydrogel and gelatin are 20% and 0.1%, respectively, by weight of the composition. Without being bound by theory, a thiol terminal, such as 1-thiol-, is used to adjust phase transition temperature. The thermoreversible gels applicable to the present invention are harmless substances which is slowly absorbed upon administration, degraded and excreted.

In one embodiment, the aqueous dispersion medium applicable to the present invention is selected from purified water suitable for administration, amino acid type, polypeptide type and pH type buffer solution. The aqueous dispersion medium applicable to the present invention is harmless, which is slowly absorbed upon administration, degraded and excreted. In another embodiment, the injectable, slow and controlled release liposome gel composition of the present invention comprises according to the weight of the composition approximately 40-90% aqueous dispersion medium, e.g. 50-80%, 60-70% or 65% by weight of aqueous dispersion medium.

In one embodiment, the present invention provides an injectable, slow and controlled release liposome composition, said composition comprises therapeutically effective amount of hypoglycemic active ingredient; 1-10% by weight of lipid, preferably phosphatyidylcholine; thermoreversible gel, said thermoreversible gel comprises 18-20% by weight of poloxamer hydrogel and 0.1-0.5% by weight of gelatin; and aqueous dispersion medium.

In one embodiment, the present invention provides a method of preparing a hypoglycemic active ingredient-containing, slow and controlled release liposome gel composition, said method comprises the following steps: mixing therapeutically effective amount of hypoglycemic active ingredient, lipid and aqueous dispersion medium to obtain lipid vesicles, liposome suspension, W/O/W type emulsion or homogeneous mixture having the hypoglycemic active ingredient loaded or dispersed therein; and emulsifying said lipid vesicles, liposome suspension, W/O/W type emulsion or homogeneous mixture by adding said lipid vesicle, liposome suspension, W/OW type emulsion or homogeneous mixture to thermoreversible gel solution; and forming liposomal microcapsule or nanocapsule, wherein said thermoreversible gel is selected from poloxamer hydrogel, thiol-terminated poloxamer, gelatin, hyaluronic acid, HA-dopamine conjugate and a combination thereof.

In one embodiment, the present invention provides a method of preparing a hypoglycemic active ingredient-containing, slow and controlled release liposome gel composition, said method comprises the following steps: mixing 0.01-2.5% by weight of hypoglycemic active ingredient, 0.05-50% by weight of lipid, and aqueous dispersion medium; forming lipid vesicles, liposome suspension, W/O/W type emulsion or homogeneous mixture at 20-40° C. to obtain a particle size ranges from 50 nm-20 µm; adding said lipid vesicles, liposome suspension, W/O/W type emulsion or homogeneous mixture to 0.05%-50% by weight of an aqueous solution of thermoreversible gel; emulsifying said lipid vesicles, liposome suspension, W/O/W type emulsion or homogeneous mixture with said aqueous solution of thermoreversible gel under 0-25° C. to form liposome microcapsule or nanocapsule. In another embodiment, the lipid vesicles, liposome suspension, W/O/W type emulsion or homogeneous mixture is prepared by a vesicular lipid gels preparation method in order to form particles of 50 nm-20 µm.

The thermoreversible gel is a transparent aqueous solution at room temperature or lower, and at 37° C. body temperature, the thermoreversible gel forms a semi-solid gel to store and slowly release the active ingredient. The thermoreversible gel suitable for use in the present invention may be poloxamer hydrogel, thiol-terminated poloxamer, gelatin, hyaluronic acid, HA-dopamine conjugate (L-DN-HA) or a combination thereof. In yet another embodiment, the thermoreversible gel is selected from poloxamer hydrogel and/ or thiol-terminated poloxamer in combination with gelatin, hyaluronic acid, HA-dopamine conjugate or a combination thereof.

In one embodiment, the present invention provides a method of preparing a hypoglycemic active ingredient-containing (such as insulin or exenatide) liposome microcapsule or nanocapsule powder formulation, said method comprises the following steps: mixing therapeutically effective amount of hypoglycemic active ingredient, 0.05-50% by weight of lipid, and aqueous dispersion medium; forming lipid vesicles, liposome suspension, W/O/W type emulsion or homogeneous mixture; adding said lipid vesicles, liposome suspension, W/O/W type emulsion or homogeneous mixture to 0.05%-50% by weight of an aqueous solution of thermoreversible gel; emulsifying said lipid vesicles, liposome suspension, W/O/W type emulsion or homogeneous mixture with said aqueous solution of thermoreversible gel to form liposome microcapsule or nanocapsule; drying said liposome microcapsule or nanocapsule to obtain the hypoglycemic active ingredient-containing liposome microcapsule or nanocapsule powder formulation. In one embodiment, the thermoreversible gel is selected from poloxamer hydrogel and/or thiol-terminated poloxamer in combination with gelatin, hyaluronic acid, HA-dopamine conjugate or a combination thereof. In another embodiment, said drying step comprises phase separation means, spray-drying means or freeze-drying means. The controlled release liposome microcapsule or nanocapsule has a high surface area for controlled release and particle size of the nanocapsule ranges from 50 nm-20 µm. Without limited by the theory, the hypoglycemic active ingredient, such as insulin or exenatide, is first released from the liposome and then released from the gel. The release of active ingredient is controlled by two barriers.

The present hypoglycemic active ingredient-containing composition may be administered subcutaneously, and by other means of parenteral administration. Preferably, the present composition is administered parenterally, for example, via intravenous, subcutaneous, intramuscular, intraperitoneal administration. In a preferred embodiment, the present invention is administered in dispersing medium.

The therapeutically effectively amount of the hypoglycemic active ingredient of the present invention may be adjusted according to the age, severity of blood glucose level and diabetes of the subject. In one embodiment, dosage of the hypoglycemic active ingredient of the present invention administered to a subject may be 0.01-100 µg/kg/day, preferably 0.05-10 µg/kg/day, said dosage may be administered in a single dose or multiple doses.

Without being bound by the theory, in one preferred embodiment of the present invention, the injectable, slow and controlled release liposome composition comprises thermoreversible composition comprising poloxamer hydrogel, thiol-terminated poloxamer, gelatin, hyaluronic acid and HA-dopamine hyaluronic acid conjugate. The components of the thermoreversible composition synergistically reduce the rate of release of the active ingredient from the liposome composition, provides good flowability at room temperature as demonstrated by the following examples below.

The examples below explain the present invention in details. The present invention is not to be limited in scope by any of the specific embodiments described herein. The following embodiments are presented for exemplification only. Unless otherwise specified, all reagents and equipment are commercially available and all components are represented by weight.

EXAMPLES

Example 1

Preparation of Exenatide or Insulin Vesicular Lipid Gel (VLG)

According to Table 1, weight exenatide (purchased from Liaoningkeitai Pharmaceutical) or insulin (purchased from Sigma Aldrich St., Louis, Mo.) (e.g. 16 mg is about 0.1% by weight), and dissolve the exenatide/insulin in HCl solution (0.01M, 69.5%) Weight phospholipids (e.g. mixed phospholipid SPC, 4.37 g, about 30 parts by weight (i.e. % by weight) and dissolve in exenatide/insulin solution and incubate in a water bath for 1 hour at 40° C. Emulsify the exenatide/insulin-phospholipid solution using a shear emulsifier at 12,000 rpm for 5 mins to form milky white semi-solid form of VLG and store the semi solid VLG at −20° C. Alternatively, the semi-solid VLG is freeze-dried to form dried lipid vesicles (FIG. 1, FIG. 1A—insulin lipid vesicles, FIG. 1B—exenatide lipid vesicles). The dried lipid vesicles are added to an aqueous medium to form lipid vesicle suspension for administration.

Example 4

Preparation of Pluronic F127 Gel Solution and, Gel Solution of Pluronic F127 with Gelatin, Hyaluronic Acid or HA-Dopamine Conjugate According to Table 2, dissolve F127 or a mixture of F127, gelatin, hyaluronic acid and HA-dopamine conjugate in

TABLE 1

Concentration (% by weight) of components of different VLG compositions and the release rate of active ingredient in vitro (the in vitro release model simulates in vivo release and is also able to analyze rate of release of different compositions.

| Composition | SPC, % | DSPE, % | Insulin, % | Exenatide, % | Aqueous medium, % | In vitro release after 1 h, % | In vitro release after 48 h, % |
|---|---|---|---|---|---|---|---|
| Vmi-1 | 20 | 0 | 10 | — | 70 | 5.32 | 6.87 |
| Vmi-2 | 30.4 | 0 | 0.1 | — | 69.5 | 3.31 | 4.85 |
| Vmi-3 | 45 | 0 | 0.1 | — | 54.9 | 2.38 | 4.10 |
| Vpi-1 | 0 | 20 | 10 | — | 70 | 4.58 | 5.38 |
| Vpi-2 | 0 | 30.4 | 0.1 | — | 69.5 | 2.39 | 3.33 |
| Vpi-3 | 0 | 45 | 0.1 | — | 54.9 | 1.42 | 2.34 |
| Vme-1 | 30 | 0 | — | 10 | 60 | 3.71 | 4.60 |
| Vme-2 | 48 | 0 | — | 2.4 | 49.6 | 1.65 | 2.47 |
| Vme-3 | 50 | 0 | — | 0.5 | 49.5 | 0.69 | 1.57 |
| Vpe-1 | 0 | 30 | — | 10 | 60 | 3.29 | 3.82 |
| Vpe-2 | 0 | 48 | — | 2.4 | 49.6 | 1.20 | 1.76 |
| Vpe-3 | 0 | 50 | — | 0.5 | 49.5 | 0.20 | 0.80 |

Example 2

Preparation of Exenatide or Insulin Liposome Suspension

Weight 1.4120 g of exenatide/insulin-containing VLG prepared according to Example 1, and using 8.558 g aqueous medium (PBS, pH-7.4; or 0.01M HCl, pH=4.01) to form approximately 10 ml exenatide/insulin-containing liposome suspension.

Example 3

Analysis of Encapsulation Efficiency and Particle Size of Exenatide or Insulin Liposome Centrifuge the liposome suspension using high speed centrifugation at 18,000 rpm, 4° C. for 30 mins to precipitate the liposomes. Adding 10 times amount of ethanol to the liposome precipitant and liposome suspension to obtain a clear liquid. Using LC-MS to measure the exenatide/insulin content in the liposome precipitate to calculate the encapsulation efficiency. The exenatide/insulin encapsulation efficiency of the liposome is 89.39±2.24%. Using Beckman coulter Delsa™Nano HC Particle Analyzer to determine the particle size of the liposome. The lipome prepared according to Example 1 has a particle size of 505±9.4 nm.

0.01M HCl (pH=4.01) or pH7.4 PBS with stirring for 24 h at 4° C. to obtain Pluronic F127 gel solution and gel solution of a mixture of Pluronic F127, gelatin, hyaluronic acid and HA-dopamine conjugate (8.558 g). The ratio of F127, gelatin, hyaluronic acid and HA-dopamine conjugate mixture is shown in Table 2.

Example 5

Preparation of Liposome Gel 1.4120 g of VLG prepared according to Example 1 is added to gel solution (8.558 g) of Pluronic F127 or F127, gelatin, hyaluronic acid and HA-dopamine conjugate prepared according to Table 2 and as described in Example 4, and subsequently add to water aqueous medium accordingly to Example 2 to form 10 ml insulin/exenatide-containing liposome gel suspension. The concentration of active ingredient, insulin or exenatide, is calculated based on Examples 1-2 and 4-5.

Using the corresponding amount of F127 or a mixture of F127, gelatin, hyaluronic acid and HA-dopamine conjugate to dissolve the corresponding amount of insulin/exenatide solution (0.01M HCl, pH4.01 or pH7.4 PBS) at 4° C. with stirring for 24 h to form insulin/exenatide gel solution as a control.

The in vitro release rate of the insulin/exenatide gel solution and insulin/exenatide containing liposome gel in 1 h and 48 h are determined. Table 2 shows % of insulin released from gel solution and liposome gel prepared based on Vmi-2 of Table 1. Other formulations in Table 1 also obtain similar results (data not shown). The liposome gel suspension is observed to have good flowability at room temperature.

TABLE 2 shows release rate of insulin in gel solution or liposome gel made of F127 or a mixture of F127, gelatin (G), Hyaluronan (Hy), HA-dopamin conjugate (LDH) of different concentrations. (the concentration in gram of F127, G, Hy and LDH are the concentration in gram of F127, G, Hy and LDH in the 10 ml of insulin gel solution and 10 ml of insulin-cotaining lipsome gel suspension.

| Formulation No. | F127 (g) | G (g) | Hy (g) | LDH (g) | In vitro release 1 h, % | | In vitro release 48 h, % | |
|---|---|---|---|---|---|---|---|---|
| | | | | | Insulin gel solution | Insulin liposome gel | Insulin gel solution | Insulin liposome gel |
| Di0 | 0 | 0 | 0 | 0 | 40.63 | 32.05 | 99.55 | 46.17 |
| Di1 | 0 | 0.5 | 0 | 0 | 29.77 | 22.95 | 67.05 | 31.89 |
| Di2 | 0 | 0 | 0.5 | 0 | 27.91 | 21.91 | 72.66 | 33.15 |
| Di3 | 0 | 0 | 0 | 0.5 | 29.25 | 22.35 | 69.02 | 33.52 |
| Di4 | 0.5 | 0.5 | 0 | 0 | 20.61 | 16.74 | 50.04 | 24.26 |
| Di5 | 0.5 | 0 | 0.5 | 0 | 21.82 | 17.49 | 50.10 | 24.24 |
| Di6 | 0.5 | 0 | 0 | 0.5 | 20.96 | 17.56 | 52.46 | 24.85 |
| Di7 | 0.5 | 0.5 | 0.5 | 0 | 16.68 | 13.52 | 41.82 | 19.86 |
| Di8 | 0.5 | 0 | 0.5 | 0.5 | 17.39 | 13.06 | 42.96 | 19.26 |
| Di9 | 0.5 | 0.5 | 0.5 | 0.5 | 14.02 | 10.77 | 33.83 | 15.79 |
| Di10 | 0.5 | 0.5 | 0.5 | 0 | 16.27 | 13.54 | 40.59 | 18.90 |
| Di11 | 0.5 | 0.5 | 0.5 | 0.5 | 14.53 | 11.41 | 35.36 | 15.50 |
| Di12 | 1.0 | 0 | 0 | 0 | 21.55 | 16.28 | 51.21 | 24.76 |
| Di13 | 1.0 | 0.5 | 0.5 | 0.5 | 11.95 | 9.82 | 31.05 | 13.28 |
| Di14 | 2.0 | 0 | 0 | 0 | 11.79 | 14.8 | 65.93 | 39.02 |
| Di15 | 2.0 | 0.5 | 0.5 | 0.5 | 5.11 | 6.17 | 26.40 | 16.35 |
| Di16 | 2.0 | 1.0 | 1.0 | 1.0 | 3.06 | 3.75 | 16.56 | 10.55 |
| Di17 | 3.5 | 0 | 0 | 0 | 12.72 | 14.92 | 71.33 | 41.15 |
| Di18 | 3.5 | 0.5 | 0.5 | 0.5 | 4.92 | 6.25 | 27.79 | 15.81 |

Table 2 shows release rate of insulin in gel solution or liposome gel made of F127 or a mixture of F127, gelatin (G), Hyaluronan (Hy), HA-dopamin conjugate (LDH) of different concentrations. (the concentration in gram of F127, G, Hy and LDH are the concentration in gram of F127, G, Hy and LDH in the 10 ml of insulin gel solution and 10 ml of insulin-containing liposome gel suspension.

Table 3 shows changes of insulin release in vitro and in vivo of insulin-containing liposome gel composition having the following content: 0.2 wt % insulin, 2 wt % DSPE, 20 wt % F127, 0.1 wt % gelatin and 77.7% PBS (pH7.4). This liposome gel composition exhibits excellent flowability at room temperature, and at 30° C. or above, this liposome gel composition is a complete gel solid. Liposome gel comprises 15 wt %, 20 wt % or 25 wt % F127 in combination with 0.05 wt % or 1 wt % gelatin or 0.05 wt %, 0.1 wt % or 1 wt % hyaluronic acid or HA-dopamin conjugate exhibits similar in vitro release profile, in vivo insulin release profile and flowability result as Table 3 (data not shown).

ExenatideDel1: liposome gel with 50 mg (0.2 wt %) exenatide and 16 g (99.8 wt %) PBS, 93% of exenatide is released after 6 hours.

ExenatideDel2: liposome gel with 50 mg (0.3 wt %) exenatide, 1 g (6.2 wt %) SPC, 15 g (93.5 wt %) PBS, 5.3% of exenatide is released after 48 hours.

ExenatideDel2: liposome gel with 50 mg (0.3 wt %) exenatide, 1 g (6.2 wt %) SPC, 15 g (93.5 wt %) PBS, 5.3% of exenatide is released after 48 hours.

ExenatideDel3: liposome gel with 50 mg (0.3 wt %) exenatide, 1 g (6.2 wt %) SPC, 3.2 g (19.9 wt %) F127, 11.8 g (73.5 wt %) PBS, 2.5% of exenatide is released after 48 hours.

Example 6

Analysis of In Vitro Release 2 ml exenatide PBS solution (pH7.4) or insulin solution (0.01M HCl, pH4.01) (the concentration of the active ingredient is based on the resultant composition), exenatide/

TABLE 3 shows changes of insulin release from lipsome gel in vitro and in vivo

| Time (hours) | 1 | 48 | 72 | 96 | 120 | 144 | 168 |
|---|---|---|---|---|---|---|---|
| % of Insulin release into Dulbecco's Phosphate Buffered saline in vitro | 6.95 | 17.32 | 29.68 | 42.77 | 59.26 | 78.34 | 95.91 |
| In vivo blood insulin concentration in rat, ng/mL | 4.5382 | 3.3933 | 2.8169 | 2.0564 | 1.3852 | 0.7523 | 0.2561 |

Table 3 shows changes of insuling release from liposome gel in vitro and in vivo Liposome gel having exenatide as the active ingredient obtained similar results. Below shows some of the experiment results:

insulin liposome suspension of Example 2, exenatide/insulin gel solution of Example 5 or exenatide/insulin liposome gel of Example 5 are placed in Mw-1000 kD dialysis bag. The sealed dialysis bag is then placed into 30 ml 0.01M PBS (pH7.4) or 0.01M HCl (pH4.01) under 36° C. water bath shaker at 50 rpm/min 1 ml of sample medium outside of dialysis bag is sampled at regular time intervals, and 1 ml of the fresh medium (i.e. PBS or HCl) is replaced. The sample medium is analyzed using LC-MS. The results are shown in Table 2 and FIG. 2 (SOL=Di0 insulin gel solution; 20% PF127=Di14 insulin gel solution; LIP=Di0 insulin liposome gel; 20% PF127-LIP=Di14 insulin liposome gel. The lower concentration of the active ingredient in the released medium demonstrates that the lower the active ingredient is being released from the test formulation, and thus slower release.

Example 7

UPLC-MS/MS Analysis

The in vitro results are obtained using UPLC (Acquity Ultra Performance Liquid Chromatography; Waters, Milford, Mass.) and MS/MS (MicroTOF-Q; Bruker Daltonics Inc, Billerica, Mass.). C18 column: column temperature=40° C.; mobile phase=0.1% formic acid in deionized water and a flow rate of 0.2 ml/min.

Example 8

Analysis of Pharmacokinetics of Insulin

Figure 3:
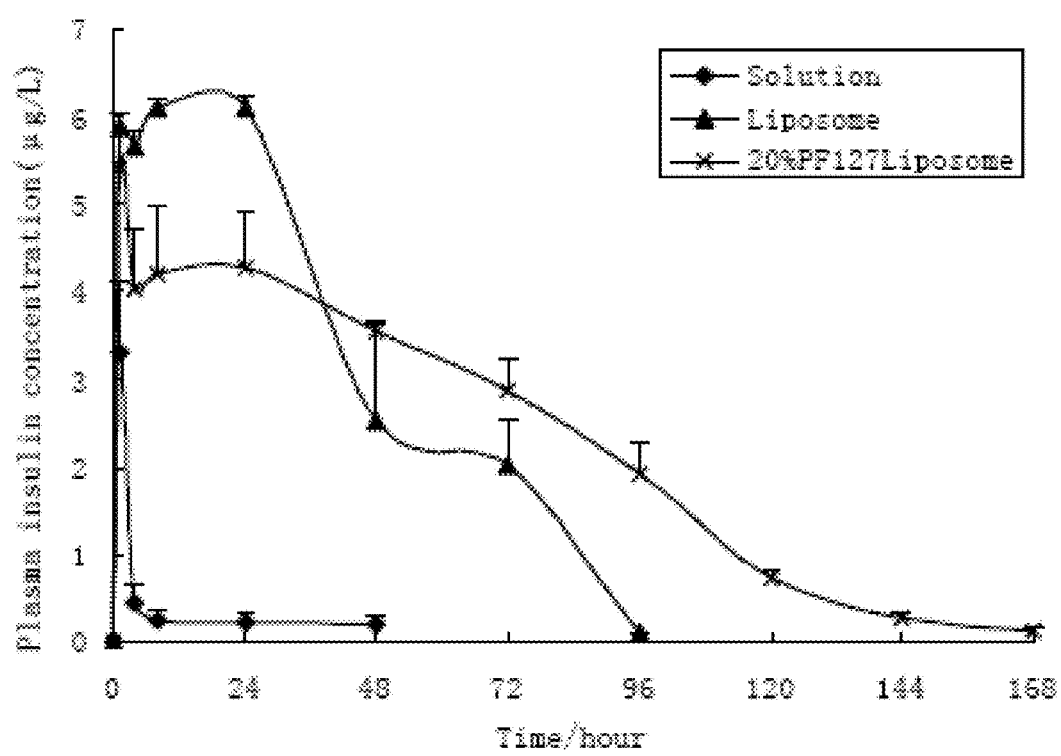
FIG. 3 shows changes of blood insulin concentration in rat for different insulin containing formulations

Randomly divide 15 rats (Sprague Dawley (SD) species; male; weight=180±20 g; purchased from Laboratory Animal Services Centre of the Chinese University of Hong Kong) into 3 groups, 5 rats in each group and fasting the rats for 14 hours, while water is available. Weight the rats after 14 hours, bovine insulin group, liposome group, or 20% F127+ liposome group are administered subcutaneously at 1 IU/kg/ day to each group of rats for 10 days. Orbital blood sampled before administration is 0 hours, after administration, orbital blood is sampled at regular time intervals and transfer to centrifuge tube having washed with 1% heparin, and centrifuge for 4 min under 4,500 rpm to separate blood plasma. The concentration of bovine insulin in rat blood plasma is analysed using ELISA test kit. The concentration of insulin in blood changes over time is shown in FIG. 3. Insulin group (SOL)=Di0 insulin gel solution in Table 2, liposome group (LIP)=Di0 insulin liposome gel in Table 2 and 20% F127 group=Di114 insulin liposome gel in Table 2.

Example 9

Analysis of Pharmacokinetics of Exenatide

Figure 4:
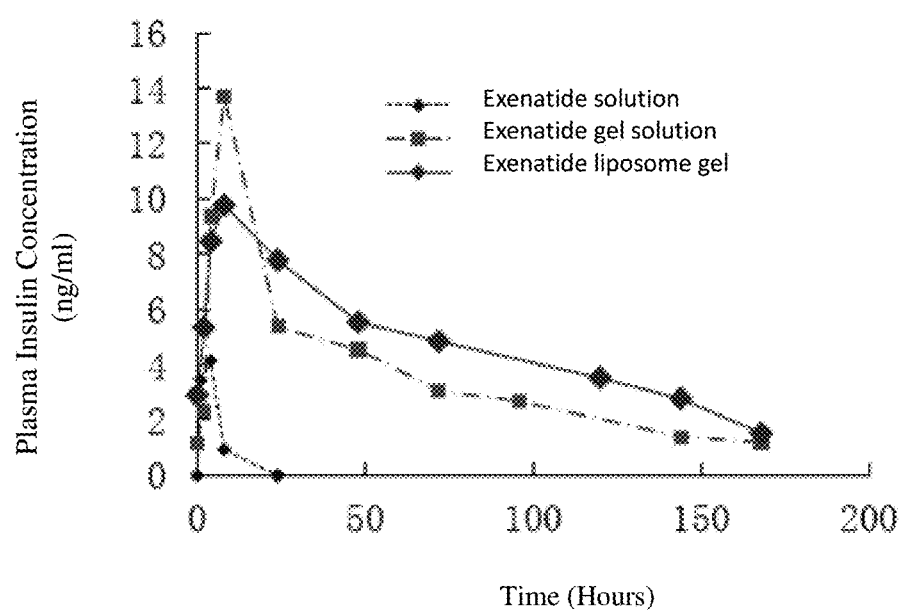
FIG. 4 shows changes of blood Exenatide concentration in rat for different Exenatide containing formulations

Randomly divide 15 rats (Sprague Dawley (SD) species; male; weight=180±20 g; purchased from Laboratory Animal Services Centre of the Chinese University of Hong Kong) into 3 groups, 5 rats in each group and fasting the rats for 14 hours, while water is available. Each group is assigned as solution group, liposome group and 20% F127 liposome group. Reweigh the rats, each group is administered with 3 mg/ml exenatide subcutaneously. Orbital blood sampled before administration is 0 hours, after administration, orbital blood is sampled at regular time intervals and transfer to centrifuge tube having washed with 1% heparin, and centrifuge for 4 min under 4,500 rpm to separate blood plasma. The concentration of exenatide in blood plasma is analysed using bovine insulin ELISA test kit. The concentration of exenatide in blood changes over time is shown in FIG. 4. In FIG. 4, the liquid exenatide=exentaide De1 composition of Example 5, exenatide liposome=exenatide De2 of Example 5 and exenatide liposome gel=exenatide De3 of Example 5.

As illustrated by the above examples, the present invention provide a novel drug delivery system being able to maintain stability of insulin or exenatide during storage and in vivo, and one single administration is capable to slowly release insulin or exenatide for 2-7 days or longer in vivo. The present invention reduces side-effects, such as pain, inconvenience and irritation, brought by the multiple administrations of insulin and exenatide. Subcutaneous administration of exenatide or insulin liposome encapsulated in temperature-sensitive polymer gel overcomes the patient compliance problems arise from the traditional requirement of multiple daily dosages.

The invention claimed is:

1. A subcutaneous slow and controlled release liposome gel composition comprising:
therapeutically effective amount of hypoglycemic active ingredient;
a lipid;
a thermoreversible gel, wherein said thermoreversible gel is a gel composition comprising a poloxamer hydrogel or a thiol-terminated poloxamer, and optionally gelatin, hyaluronic acid, hyaluronic acid-dopamine conjugate or a combination thereof and said lipid is soybean phosphatidylcholine (SPC); and
an aqueous dispersion medium.

2. The composition of claim 1, wherein said thermoreversible gel composition comprises poloxamer hydrogel and does not contain gelatin, hyalunronic acid, hyaluronic acid-dopamine conjugate or a combination thereof.

3. The composition of claim 1, wherein said thermoreversible gel composition comprises poloxamer hydrogel in combination with gelatin, hyaluronic acid, and hyaluronic acid-dopamine conjugate.

4. The composition of claim 1, wherein the liposome gel composition comprises 0.05-50%, 0.5-35%, 1-20%, 5-15% or 10-12% by weight of thermoreversible gel.

5. The composition of claim 3, wherein the liposome gel composition comprises 10-30% and 0.05-2%, 15-25% and 0.08-1%, 18-20% and 0.1-0.5% or 20% and 0.1% by weight of poloxamer hydrogel and gelatin, hyaluronic acid, hyaluronic acid-dopamine conjugate or a combination thereof, respectively.

6. The composition of claim 1, wherein the liposome gel composition comprises 0.05-50%, 0.7-30%, 1-20%, 1-10% or 2-5% by weight of lipid.

7. The composition of claim 1, wherein said hypoglycemic active ingredient is insulin, Exenatide, Liraglutide, Pramlintide or a combination thereof.

8. The composition of claim 1, wherein said poloxmaer hydrogel is poly(ethylene glycol)-block-poly(propylene glycol)-block-poly(ethylene glycol) having an average molecular weight of 12,600 Daltons or poly(ethylene glycol)-block-poly(propylene glycol)-block-poly(ethylene glycol) having an average molecular weight of 5,800 Daltons.

9. The composition of claim 1, wherein said aqueous dispersion medium is selected from purified water suitable for administration, amino acid buffer, polypeptide buffer and pH buffer.

10. The composition of claim 1, wherein the liposome gel composition comprises 0.01-2.5% by weight of hypoglycemic active ingredient.

11. The composition of claim 7, wherein said insulin is selected from insulin analogue, human insulin, animal insulin or a combination thereof.

12. The composition of claim 7, wherein said Exenatide is selected from Exendin-3, Exendin-4, C-terminal amide substituted Exenatide derivative, non-substituted Exenatide derivative and pharmaceutically acceptable salts thereof.

13. The composition of claim 7, wherein the lipid comprises liposomes having a particle size of 50nm-20 μm, in a lipid suspension, W/O/W type emulsion or homogeneous mixture; said hypoglycemic active ingredient is loaded or dispersed in said liposome and said hypoglycemic active ingredient loaded or dispersed in said liposome is loaded in said thermoreversible gel.

14. The composition of claim 1, wherein said liposome gel composition is capable of releasing the hypoglycemic active ingredient for 2-7 days or longer in vivo.

15. A method of preparing a hypoglycemic active ingredient-containing, slow and controlled release liposome gel composition, said method comprises:

mixing a therapeutically effective amount of a hypoglycemic active ingredient, a lipid and an aqueous dispersion medium to form vesicular lipid gel, lipid suspension, W/O/W type emulsion or homogeneous mixture having hypoglycemic active ingredient loaded or dispersed therein; and adding said vesicular lipid gel, lipid suspension, W/O/W type emulsion or homogeneous mixture to a thermoreversible gel for emulsification to folio a liposome gel, wherein said thermoreversible gel is a gel composition comprising a poloxamer hydrogel or a thiol-terminated poloxamer, and optionally gelatin, hyaluronic acid, hyaluronic acid-dopamine conjugate or a combination thereof and said lipid is soybean phosphatidylcholine (SPC).

16. The method of claim 15, wherein said thermoreversible gel composition comprises a poloxamer hydrogel and does not contain gelatin, hyaluronic acid, hyaluronic acid-dopamine conjugate or a combination thereof.

17. The method of claim 15, wherein said thermoreversible gel composition comprises poloxamer hydrogel in combination with gelatin, hyaluronic acid, and hyaluronic acid-dopamine conjugate.

18. The method of claim 15 further comprises drying the liposome gel to obtain hypoglycemic active ingredient-containing liposome gel powder.

19. A hypoglycemic active ingredient-containing liposome gel or liposome gel powder prepared according to method of claim 15.

* * * * *